(12) United States Patent
Amir

(10) Patent No.: US 10,593,187 B2
(45) Date of Patent: Mar. 17, 2020

(54) APPARATUS COMPRISING A BED PROXIMITY-DETERMINING SYSTEM

(71) Applicant: CenTrak, Inc., Newtown, PA (US)

(72) Inventor: Israel Amir, Princeton, NJ (US)

(73) Assignee: CenTrak, Inc., Newtown, PA (US)

( * ) Notice: Subject to any disclaimer, the term of this patent is extended or adjusted under 35 U.S.C. 154(b) by 0 days.

(21) Appl. No.: 15/919,747

(22) Filed: Mar. 13, 2018

(65) Prior Publication Data
US 2018/0276973 A1 Sep. 27, 2018

Related U.S. Application Data

(60) Provisional application No. 62/601,175, filed on Mar. 13, 2017.

(51) Int. Cl.
G08B 21/22 (2006.01)
G01S 11/06 (2006.01)
G05B 15/02 (2006.01)
G01S 11/16 (2006.01)
G16H 40/63 (2018.01)
G08B 21/24 (2006.01)
G01S 5/30 (2006.01)

(52) U.S. Cl.
CPC ............ G08B 21/22 (2013.01); G01S 11/06 (2013.01); G01S 11/16 (2013.01); G05B 15/02 (2013.01); G16H 40/63 (2018.01); G01S 5/30 (2013.01); G08B 21/245 (2013.01)

(58) Field of Classification Search
USPC .................. 340/12.1–12.55, 539.1–539.23
See application file for complete search history.

(56) References Cited

U.S. PATENT DOCUMENTS

| | | | | |
|---|---|---|---|---|
| 6,078,253 A * | 6/2000 | Fowler | ............... | G06K 9/00335 307/116 |
| 7,911,348 B2 * | 3/2011 | Rodgers | ................. | G06Q 30/02 340/573.1 |
| 7,987,069 B2 * | 7/2011 | Rodgers | ................ | A61B 5/1115 702/150 |
| 8,054,160 B2 * | 11/2011 | Corrado | ............. | G06K 19/0723 340/10.1 |
| 2002/0014951 A1 * | 2/2002 | Kramer | ................ | A61B 5/0002 340/5.8 |
| 2008/0015903 A1 * | 1/2008 | Rodgers | ................. | G06Q 30/02 705/3 |
| 2015/0206415 A1 * | 7/2015 | Wegelin | ............... | G08B 21/245 340/573.4 |
| 2016/0026837 A1 * | 1/2016 | Good | ..................... | H04W 4/02 340/539.13 |
| 2017/0035370 A1 * | 2/2017 | Collins, Jr. | ........... | A61B 5/1115 |

* cited by examiner

Primary Examiner — Emily C Terrell
Assistant Examiner — Sharmin Akhter
(74) Attorney, Agent, or Firm — Kaplan Breyer Schwarz, LLP

(57) ABSTRACT

A bed proximity-determining system includes communications functionality and an ability to determine the proximity of a caregiver to a bed. Based on that proximity, the system transmits commands to the bed or a local system.

27 Claims, 8 Drawing Sheets

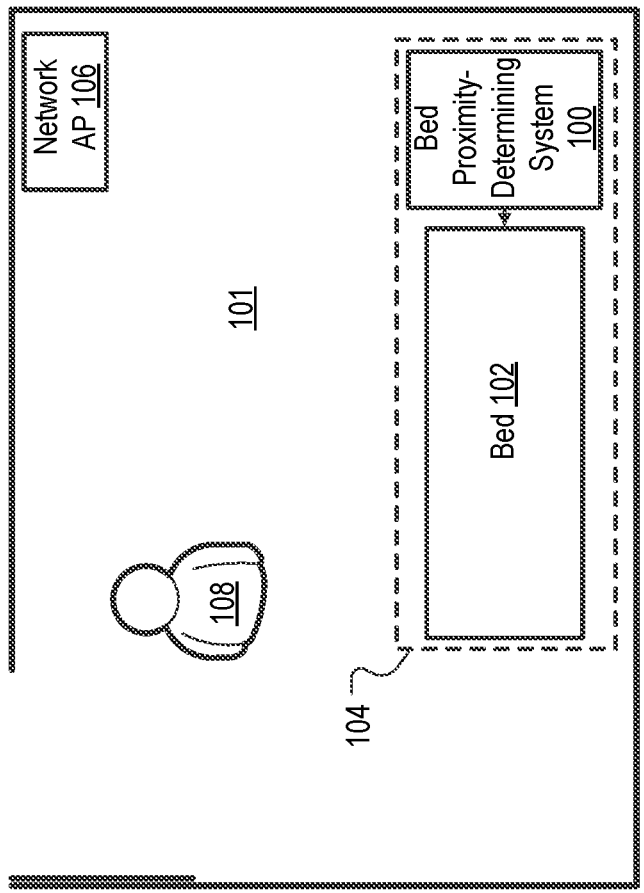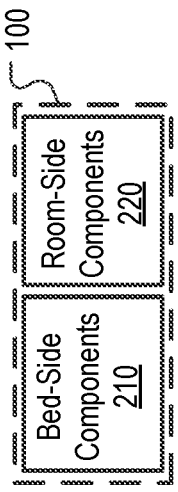

APPARATUS COMPRISING A BED PROXIMITY-DETERMINING SYSTEM

STATEMENT OF RELATED CASES

This case claims priority of U.S. Pat. Application Ser. No. 62/601,175 filed Mar. 13, 2017, which is incorporated herein by reference.

BACKGROUND

In the last couple of decades, advances in information technologies, wireless networking, and sensor technologies have made their way into healthcare. The presence of such technologies is reflected, for example, in the federal electronic medical records (EMR) mandate, the rise of networked diagnostic devices, hospital asset tracking, wireless sensors for patient monitoring, and security systems.

The incorporation of such technologies to more and more aspects of patient care provides benefits to patients, caregivers, and health-care facilities managers alike.

SUMMARY

Embodiments of the invention provides a bed proximity-determining system, a bed incorporating the bed proximity-determining system, and a method for transmitting information to a suitably configured bed or other local systems based on the proximity of a caregiver.

Sensor-enabled beds that determine the presence of a patient in a bed are known. They are used to monitor patient movements, often for safety reasons, such as fall monitoring. The present inventors recognized that there are potential benefits for determining the proximity of a caregiver to the bed.

In accordance with some embodiments of the system and method, certain bed-based functions, or functions of other in-room systems, are activated based on the proximity of a caregiver to a bed. For example, when a caregiver is in very close proximity to the bed (c.a. 2-3 feet), the system and method can result in the activation of certain bed-based functions, such as, for an appropriately configured bed, releasing/activating a fall-prevention lock for the bed rails. Also, the system and method can result in the activation of a hand-hygiene warning, as appropriate. In some embodiments, certain functions can be activated when a caregiver is in the vicinity of the bed (c.a. 5-15 feet), but not necessarily as close as discussed above. Examples of such other functions include call cancelation or local asset tracking.

It is notable that there are existing systems that can identify the presence of a particular bed in a specific room, typically for asset-tracking purposes. But such systems lack the ability to resolve proximity, in particular the proximity of a caregiver, with the accuracy necessary for embodiments of the present invention.

The bed proximity-determining system includes devices that have communications functionality, proximity-determining functionality, or both. Some of the devices are physically coupled to the bed, such that they will move with the bed (e.g., if the bed is moved to various locations in the healthcare facility). Some other of the devices of the system are room-based.

The system incorporates a mobile tag that is worn by a caregiver, wherein the tag includes communications capabilities and, optionally, processing capability. The system also includes devices, each including one or more of transmitters, receivers, and processors, wherein the devices are coupled to a patient bed and or located elsewhere in the patient room. Collectively, the elements of the system enable the tag to estimate its proximity to a patient bed and report that proximity, or information based thereon, to other elements of the system.

The proximity determination can be based on the transmission of ultrasound, which results in an estimated distance from the location of one or more ultrasound transmitters, which in various embodiments are located on a wall in the patient room, on the patient bed, or both. Proximity determination can also be based on LF sensing, which typically, although not necessarily, provides a qualitative, rather than quantitative proximity determination.

Based on the proximity determination, elements of the system determine what action, if any, should be taken with respect to the bed or other local systems. In some embodiments, elements of the system issue commands or a control signal to actuate a mechanism; in some other embodiments, elements of the system simply report distance to local systems, wherein such local systems make a determination of how to respond based on their own programming. For example, such actions include, without limitation: transmitting a command to cancel a call to a caregiver call system, reporting the location of the bed to a local network, releasing a fall-prevention lock on a bed rail, and reporting distance or a command to a hand-hygiene alert system. Embodiments of the invention are now discussed with further specificity.

In a first embodiment, the system and method utilizes low frequency RF (LF), infrared (IR), short-distance wireless (SRD), and possibly ultrasound (US) components for communications and proximity determination. Elements of this embodiment include, among any others:

A tag, wherein the tag is worn by the caregiver and includes a variety of communications (IR, US, LF, SRD, wireless) and processing capabilities.

An IR/US emitter, wherein a device including an IR emitter and an US emitter ("IR/US emitter") is installed in patient rooms in a health-care facility. Alternatively, the IR emitter and the US emitter can be two discrete devices installed in patient rooms. In some embodiments, a room identifier (ID) is periodically transmitted via the IR emitter. In some embodiments, the IR signal from the IR emitter provides timing information. Ultrasound from the US emitter is used for proximity determination. In a variant, a US/US emitter is used, wherein both the ID transmission and proximity determination is performed using US. It is to be understood that all references herein to the use of an IR/US emitter are understood to include the alternative embodiment of an US/US emitter. The term "signal," as used herein, is not meant to require that information is being conveyed. In particular, in many embodiments, the ultrasound being transmitted does not contain any data, etc.

LF exciters, wherein the LF exciters are physically coupled to the bed or placed directly beneath or alongside the bed. The LF exciters emit an LF field having a typical frequency of 125 kHz.

An SRD transceiver and IR receiver, which can be an integrated device or two physically separate components, both of which are collectively referred to as an "SRD/IR device," are physically coupled to the bed or placed directly alongside it. The IR receiver receives IR communications, such as from the IR/US emitter. The SRD transceiver performs several tasks, including receiving communications from the tag, (optionally) controlling the LF exciters, and communicating with the bed controller or other local systems.

A bed controller, wherein the controller is physically coupled to the bed and, based on commands or information it receives from the SRD/IR device, controls bed functions.

In the first embodiment, when a bed is wheeled into a room, the SRD/IR device detects the room ID, as transmitted by the IR/US emitter (or network) and associates it with the bed. Using the tag's IR receiver and US receiver, in some implementations, the tag estimates it distance to the IR/US emitter. In some implementations, the tag transmits, to the SRD/IR device, the estimated distance. In some other implementations, rather than transmitting the estimate distance, the tag transmits, to the SRD/IR device either: information from which distance can be calculated or commands to take certain action. In some additional implementations, the tag reports any of the aforementioned distance, information, or commands to the bed controller. In some other implementations of the first embodiment, the tag transmits directly to other local systems, such the call system or a hygiene alert system, for action, and devices in those systems determine how to respond.

Regardless of which device—the tag, the SRD/IR device, the bed controller, devices in other local systems—determines how to respond to the distance information, the determination depends on the estimated proximity of the tag to the bed.

For example, in excess of certain distance, say 15 feet, the tag, depending on its programming, might not transmit any information (e.g., neither distance nor a command, etc.) to any of the other devices. Or, if distance is transmitted from the tag to the SRD/IR device, the latter device might determine, based on its programming, not to transmit any information to the bed controller or other local systems. Alternatively, either the tag or SRD/IR device might transmit a message (e.g., to the bed controller, etc., that no action should be taken).

At some intermediate distance say, 5-15 feet, in some implementations of the first embodiment, the tag, depending on its programming, sends distance information or a command to the SRD/IR device, bed controller, or directly to a local system. In some implementations, the SRD/IR receives distance information from the tag, and then sends either distance information or a command to the bed controller or a local system.

As the tag moves increasingly closer to the bed, the tag detects the LF field emanating from the LF exciter(s). When it does, in some implementations of the first embodiment, the tag sends a message to the SRD/IR device that the LF field has been detected/breached, or sends a command or other guidance to the SRD/IR device, bed controller, or directly to local systems. For example, at this distance, the tag or SRD/IR device, with knowledge that the LR field has been detected, may send a command to the bed controller to unlock the fall prevention locks of the bed rails. Also, as appropriate, the tag or SRD/IR device sends a command to activate an alert (or send information to an alert system that then makes the activation decision) if the approaching caregiver has not washed his hands. Preferably, the tag is configured to detect hand-hygiene events (i.e., the fact that the caregiver has or has not washed his hands at the appropriate time/opportunity).

In a second embodiment, the system utilizes IR, US, and SRD, but not LF. Elements of this embodiment include some of the aforementioned elements, including the tag, the IR/US emitter, the SRD/IR device, and the bed controller. The LF exciters are not used; rather, at least one pair, and preferably two or more pairs of US transmitters are used for proximity determination. In some embodiments, the wall mounted IR/US emitter is used for transmitting the room ID over IR and for transmitting timing information related to initiating the signaling from the two pairs of US transmitters.

In both of the aforementioned embodiments, as desirable, the bed proximity-determining system can be configured to communicate, such as over 802.11, 900 MHz, or other protocols, with a local network. The local network can be used to convey timing information, and, more generally, receive or convey wireless reporting to the system to regarding location, status, wireless upgrades as well as command, control, and modification of operational profiles. Thus, timing information can be transmitted from the network to the IR/US transmitter, to the SRD/IR device, or to the tag. In some embodiments, wavelengths other than IR are used for signaling that, in the illustrative embodiment, is accomplished via IR. In such embodiments, IR transmitters and receivers will be replaced by transmitters and receivers for such other frequencies.

An embodiment of the invention comprises a bed proximity-determining system, wherein the bed proximity-determining system includes:

(1) a first infrared transmitter for transmitting an infrared signal, wherein the first infrared transmitter is associated with and is physically coupled to a surface of a room;

(2) one or more ultrasound transmitters that transmit ultrasound;

(3) a tag, the tag having an IR receiver for receiving the infrared signal, an ultrasound receiver for receiving ultrasound from the one or more ultrasound transmitters, and a transmitter that transmits first proximity-related information based on the received ultrasound;

(4) a first transceiver that receives the first proximity-related information and either:
  (a) transmits the first proximity-related information, or
  (b) generates and transmits second proximity-related information that is based on the first proximity-related information; and (5) a bed controller, wherein the bed controller receives the first proximity-related information or second proximity-related information, and performs at least one of the following actions:
  (a) generates a control signal based on the first or second proximity-related information;
  (b) generates a command based on the first or second distance-proximity information; or
  (c) transmits the first or second proximity-related information.

The first proximity-related information can be (i) information that can be used to determine a distance, (ii) a determined distance, (iii) qualitative estimate of distance, or (iv) an instruction or command based on the determined distance or qualitative estimate of distance. The second proximity-related information is either (ii) or (iv) when the first proximity-related information is (i).

BRIEF DESCRIPTION OF THE DRAWINGS

FIG. 1 depicts an article comprising a bed proximity-determining system in accordance with the illustrative embodiment of the present invention, wherein the article is in a health-care environment.

FIG. 2 depicts further detail of the bed proximity-determining system of FIG. 1.

DETAILED DESCRIPTION

Figure 3:
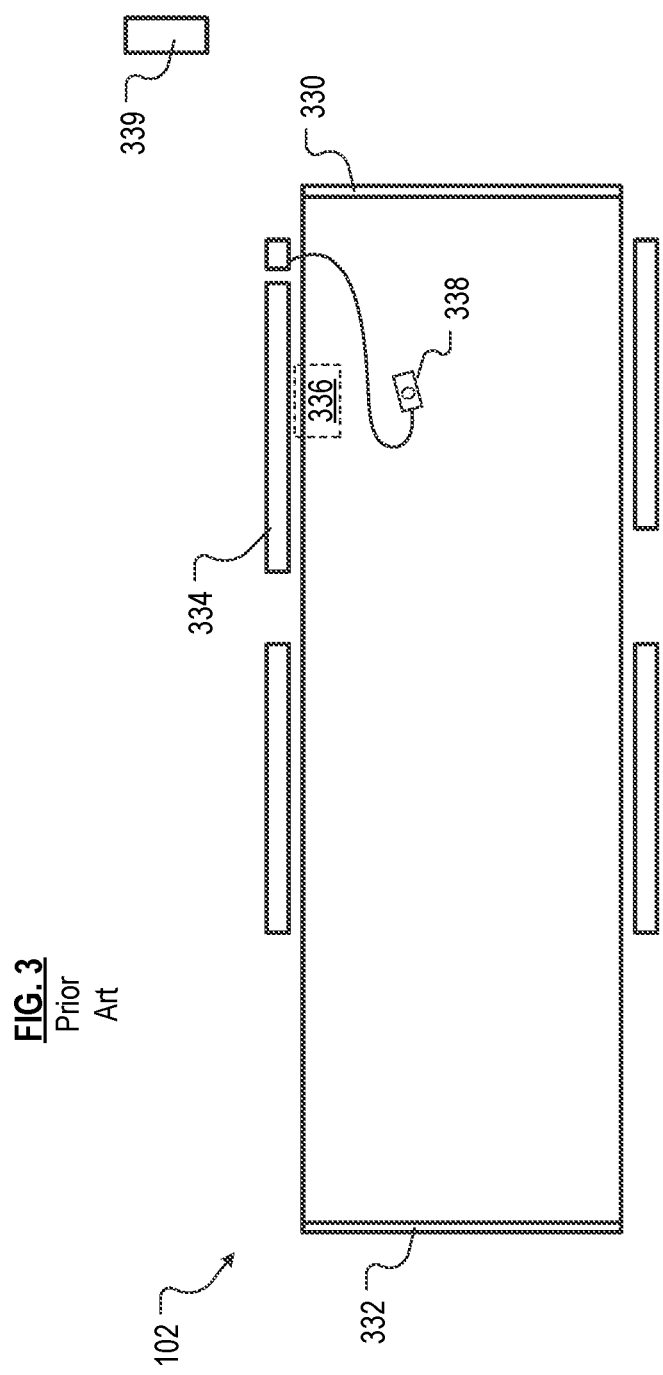
FIG. 3 depicts further detail of the article of FIG. 1.

The following definitions are to be used in this disclosure and the appended
- "transmitter" is a device, circuit, or apparatus capable of transmitting an electrical, electromagnetic, infrared, ultrasonic, or optical signal.
- "receiver" is a device, circuit, or apparatus capable of receiving an electrical, electromagnetic, infrared, ultrasonic, or optical signal.
- "transceiver" is a device, circuit, or apparatus capable of transmitting and/or receiving an electrical, electromagnetic, infrared, ultrasonic, or optical signal.
- "US" means "ultrasound".
- "IR" means "infrared".
- "Proximity-related information" means (i) information that can be used to determine a distance, (ii) a determined distance, (iii) a qualitative estimate of distance, or (iv) an instruction or command based on the determined distance. With respect to item (iii), what is meant by a "qualitative" estimate of distance is that an estimated distance is inferred based on the detection of an event. For example, the detection of LF field that emanates from an LF exciter represents a qualitative estimate of distance, since the field is detectable from no more than about 2 to 3 from its source.

FIG. 1 depicts apparatus 104, which is an enhanced bed in accordance with the present teachings. FIG. 1 depicts apparatus 104 in a healthcare setting, such as hospital room 101.

Apparatus 104 includes bed 102 and bed proximity-determining system 100. The bed proximity-determining system is capable of sensing the proximity of caregiver 108 and triggering certain bed-related functions or triggering action in other local systems (e.g., hygiene system, a call system, etc.). In some embodiments, some modifications are performed to a conventional hospital bed for use in conjunction with embodiments of the invention. For example, some otherwise manual features are modified to enable automatic/motorized operation in conjunction with bed proximity-determining system 100. Thus, bed 102 may be, but not necessarily will be, modified, as discussed in conjunction with FIG. 3. In some embodiments, a local wireless network is accessed, such as via network access point 106, to support communications to and from bed proximity-determining system 100.

As depicted in FIG. 2, bed proximity-determining system 100 includes bed-side components 210 and room-side components 220. In some embodiments, bed-side components 210 are physically coupled to and remain with the bed. The bed-side and room-side components are discussed further below in conjunction with FIGS. 4, 6A, 6B, 7 and 8.

FIG. 3 depicts salient elements of bed 102. The bed includes headboard 330 footboard 332, side rails 334, and actuator(s) 336. Call button 338, accessible from a patient's bed, is part of call system 339. The call system, which can be wired or wireless, enables communication between a patient and nurse, in addition to providing other capabilities.

In the illustrative embodiment, actuator(s) 336 (only one is depicted) are controlled via elements of bed proximity-determining system 100 to unlock the locking mechanism (fall-prevention lock) for each side rail 334. It is notable that actuator(s) 336 are present in existing advanced beds. To the extent that other functions of the bed are to be actuated based on proximity (or voice command) in accordance with the invention, it may be necessary to add additional elements (e.g., actuators, motors, etc.) to bed 102.

Figure 4:
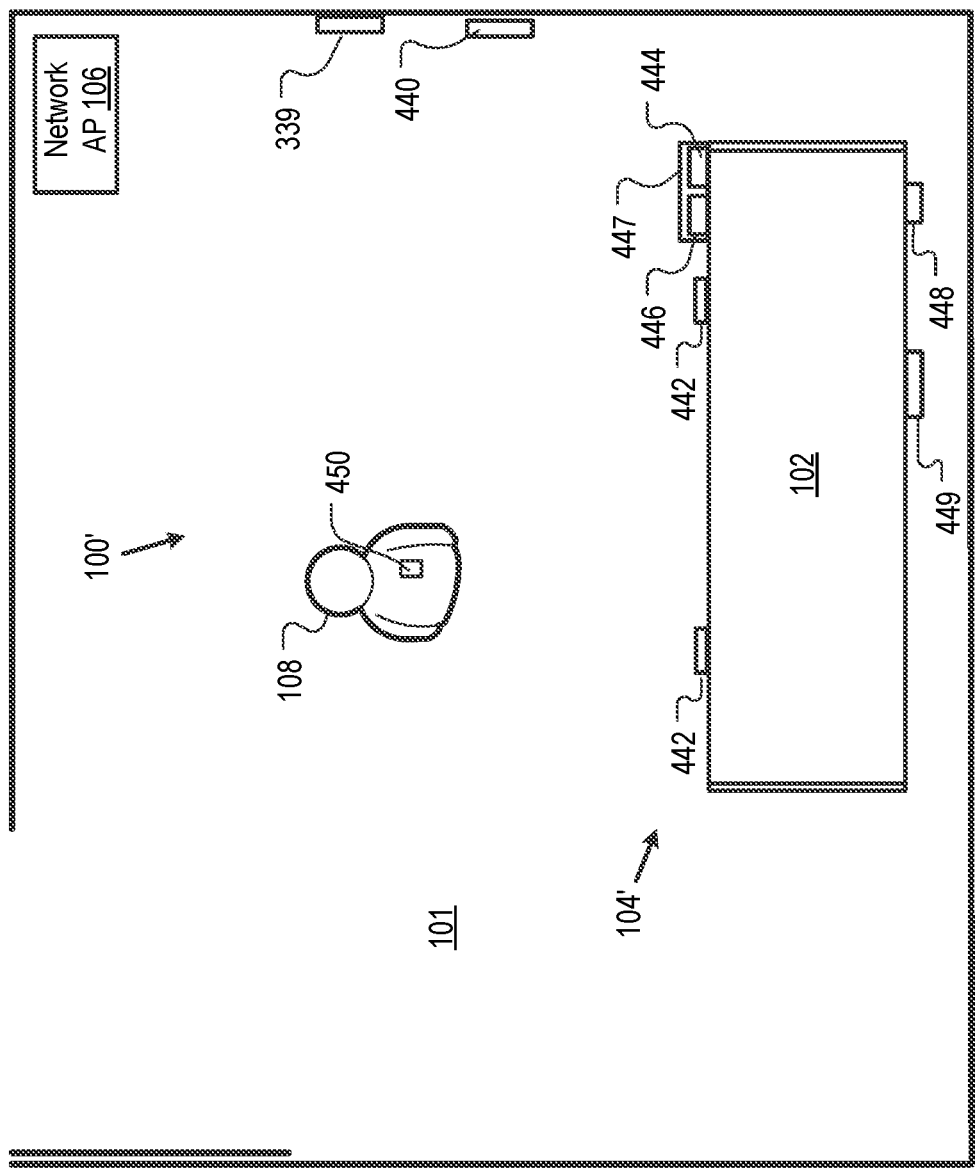
FIG. 4 depicts a first embodiment of the article of FIG. 1.

FIG. 4 depicts apparatus 104', including bed proximity-determining system 100' and bed 102. This embodiment of the bed proximity-determining system 100' includes IR/US emitter 440, LF exciters 442, IR receiver 444, SRD transceiver 446, bed controller 448, and tag 450. In the illustrative embodiment, IR receiver 444 and SRD device 446 are integrated in SRD/IR device 447. In the embodiment depicted in FIG. 4, LF exciters 442, SRD/IR device 447, and bed controller 448 are bed-side components 210. IR/US emitter 440 and tag 450 are room-side components 220.

In some embodiments, IR/US emitter 440 includes an IR transmitter and a US emitter. In the embodiment discussed in FIGS. 4, 6A, 6B, IR/US emitter 440 has two functions: (1) periodically transmit the room ID and (2) proximity determination. Typically, although not necessarily, the ID is transmitted via an IR signal from the IR transmitter. And the ultrasound is used for proximity determination. The IR signal additionally provides timing for the ultrasound. In some embodiments, IR/US (or US/US) emitter 440 also includes a wireless communications device that enables communications with a network. The wireless communications device also enables wireless synchronization with other elements of the bed command system (e.g., other IR/US emitters in the room, other US emitters as used in other embodiments discussed herein, etc.) for various purposes, as previously noted. IR/US emitter 440 is typically attached to a wall, near the ceiling, in room 101.

Well-known in the art, LF exciter(s) 442 (two are depicted in FIG. 4, although fewer or more could be used) emit a LF field that extends for about 2 to 3 feet. LF exciters 442 are attached to bed 102, typically on the long side that a caregiver will approach, hereinafter referred to as the "forward edge" of the bed. Alternatively, the LF exciters may be positioned alongside of and aligned with, but not attached to, the forward edge of the bed.

IR receiver 444 (integrated in the illustrative embodiment into SRD/IR device 447) is configured to receive the ID signal transmitted from IR/US emitter 440 (assuming that the ID is being transmitted via IR). This enables bed 102 to associate with room 101. This is useful for asset-tracking purposes wherein in some embodiments, the SRD transceiver 446 or other receiver in SRD/IR device 447, can report the bed-to-room association to the health-care facility's network via network AP 106. IR receiver 444 is typically, but not necessarily, attached to bed 102.

SRD transceiver 446 (integrated in the illustrative embodiment into SRD/IR device 447), is a short-range communications device, such as, without limitation, a Bluetooth low-energy transceiver, a WiFi transceiver, or a transceiver operating in one of the ISM bands. SRD transceiver 446 receives communications and commands from tag(s) 450, either directly or via network communications. Also, in some embodiments, SRD transceiver 446 or another receiver in SRD/IR device 447, receives timing information, such as concerning IR signaling, from the health-care facility's network. SRD transceiver 446 (or SRD/IR device 447) is typically, but not necessarily, attached to bed 102.

In some embodiments, suitable programming is incorporated into SRD transceiver 446 (or is otherwise part of SRD/IR device 447) for making decisions/issuing commands based on the tag's estimated distance/proximity. These communications and commands are directed to bed controller 448 to control predefined bed functions, or call system 339 (such as to cancel a call, etc.) or hygiene system 449. In some other embodiments, SRD/IR device 447 receives decisions/commands from tag 450, and simply forwards them to the appropriate device/system.

Hygiene system 449, which in some embodiments includes a receiver, processor, and speaker, issues an audible alert if it receives a command or information that indicates that an approaching care-giver has not followed hygiene guidelines (i.e., not washed their hands at an appropriate time). In some embodiments, the alert is received by a device carried by the caregiver that, rather than issuing an audible alert, will vibrate, etc., such that only the caregiver is aware of the infraction.

Bed controller 448 receives signals from tag 450 or SRD/IR device 447. In various implementation of this first embodiment, the decision to take action can be reached by tag 450, SRD/IR device 447, or bed controller 448. Thus, in some implementations, the signal received by the bed controller will include a proximity estimate, such that decision making is left up to bed controller 448, based on programmed guidelines for the type of action required as a function of the estimated proximity of tag 450. And, in some other implementations, bed controller receives a command from tag 450 or SRD/IR device 447 and converts that command into an appropriate control signal. In either case, bed controller 448 transmits the control signal to a bed mechanism, such as an actuator of a lock, for unlocking a bed rail.

In some implementations, hygiene system 449 is physically coupled to the bed and is controlled by bed controller 448. Thus, as appropriate, the bed controller will transmit information to hygiene system 449. In some implementations, the information will include tag proximity and whether or not the proper hygiene was followed, leaving decision-making up to hygiene system 449. In some other implementations, bed controller 448 transmits instruction/commands to hygiene system as to whether to issue an alert.

Existing advanced beds will include a controller for use in conjunction with certain functions (e.g., weigh scale, "up" and "down" movement of the mattress support, etc.). As such, the existing controller can be re-programmed for use in conjunction with embodiments of the invention, so as to function as bed controller 448. Because such re-programming is likely to require new FDA approval, it is preferable for bed proximity-determining system 100' to include bed controller 448, which is distinct from any controller provided as part of bed 102.

In some implementations, all bed-side device 210 are wired to facilitate control and command by SRD/IR device 447 and/or bed controller 448.

Figure 5:
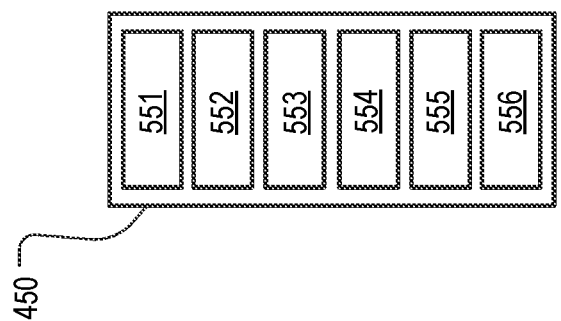
FIG. 5 depicts an embodiment of a tag used in conjunction with the article of FIG. 4.

Communications tag(s) 450 are worn by caregivers. As depicted in FIG. 5, tag 450 includes, in addition to any other functionality, IR receiver 551, US receiver 552, LF receiver 553, motion sensor 554, SRD transmitter 555, and network wireless transceiver 556. Motion sensor 554 is used to reduce power consumption (i.e., to shut off receivers/transceivers when the tag/caregiver is not moving). The tag will also include, in some embodiments, a processor, suitably programmed for proximity estimation and/or decision-making based on the proximity estimate. The use of the various receivers and transceivers are explained in conjunction with FIGS. 6A and 6B.

Figure 6A:
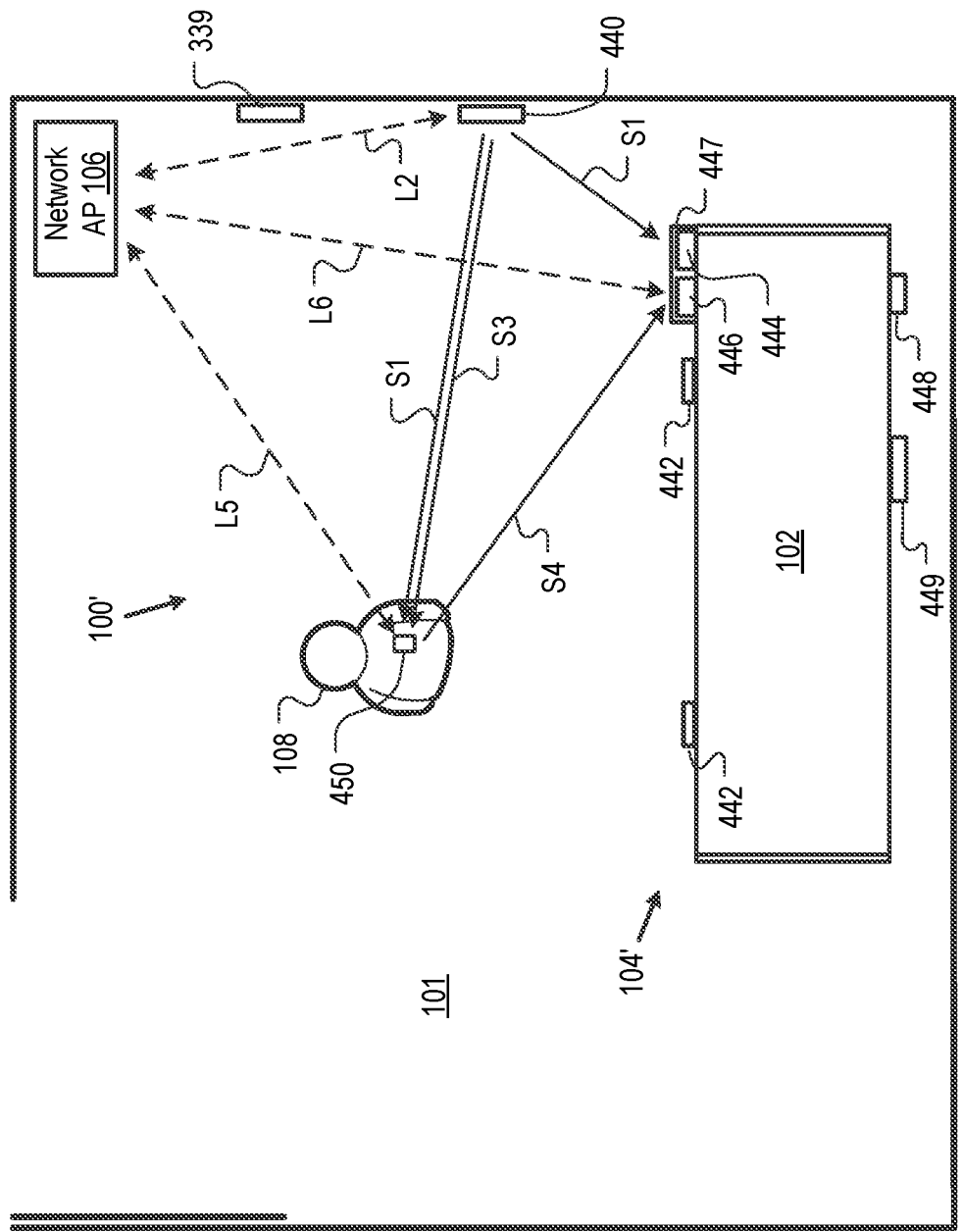
FIG. 6A depicts signaling for the embodiment depicted in FIG. 4 when a communications tag is well outside of the range of LF exciters.

FIG. 6A depicts an embodiment of the signaling occurring in conjunction with use of bed proximity-determining system 100' when tag 450 is well outside of the range of LF exciters 442.

IR/US emitter 440 periodically transmits IR signal S1, which carries the room/device ID. Signal S1 is received by IR receiver 444 of SRD/IR device 447 and by IR receiver 551 on tag 450. In some embodiments, SRD/IR device 447 reports the association of the bed with the ID (i.e., the particular room) to the local network via network AP 106 over communications link L6 (communications links are bi-directional).

At the same time, or at a known time after the transmission of signal S1, IR/US emitter 440 transmits ultrasound S3, typically as a short burst. Using its IR receiver 551 and US receiver 552, tag 450 can estimate its distance to IR/US emitter 440. In particular, knowing when the ultrasound burst S3 was transmitted, and the speed at which US travels in air (about 331.4 meters/sec), the distance between tag 450 (i.e., the caregiver) and the IR/US emitter 440 is calculated by the tag. Since IR signal S1 travels at the speed of light, an in light of relatively short distances involved, it is assumed that the receive time of signal S1 at tag 450 is the same as its transmission time from IR/US emitter 440.

In embodiments in which signal S1 and ultrasound transmission S3 are transmitted simultaneously, the time at which ultrasound transmission S3 was transmitted is therefore considered to be the time at which IR signal S1 is received at tag 450. If ultrasound S3 is transmitted with some delay relative to signal S1, then the time at which the ultrasound was transmitted is considered to be the time at which IR signal S1 is received plus the aforementioned delay. The delay, which in some embodiments is controlled by the network, can be communicated directly to IR/US transmitter 440 via communications link L2 and directly to tag 450 via communications link L5. Or such timing information can originate with IR/US transmitter 440 and be transmitted therefrom to one or both of tag 450 and SRD/IR device 447.

The distance between tag 450 and IR/US emitter 440, which in some implementations is calculated by tag 450, is then transmitted by signal S4, such as via the tag's SRD transmitter 555, to SRD device 446 in SRD/IR device 447. In some other embodiments, the distance is reported to the network over communications link L5, and from the network to SRD/IR device 447 via link L6. As previously noted, rather than estimating and transmitting distance, tag 450 can transmit data required for estimating distance or transmit instructions/commands based on the estimation of distance.

If the distance between the tag and IR/US emitter 440 is greater than some threshold distance, such as 15 feet:
  Tag 450, as a function of its programming, might not report any information to SRD/IR device 447 or any other part of the system.
  In some other implementations, assuming SRD/IR device 447 receives distance or the information required for its calculation, it might, as a function of its programming, not report to bed controller 448 or any other part of the system.

If the distance between the tag and IR/US emitter 440 is less than a specified distance, for example less than 15 feet:

Tag 450, as a function of its programming, will transmit proximity-related information to SRD/IR device 447, or bed controller 448, or other local systems, such as to take certain actions (e.g., to call system 339 to cancel a call, to hygiene system 449 to issue an alert, etc.).

If Tag 450 transmits to SRD/IR device 447, that latter will, based on its programming, transmit proximity-related information (e.g., distance, a command, etc.) to controller 448 or other local systems to take certain actions, as indicated above.

Figure 6B:
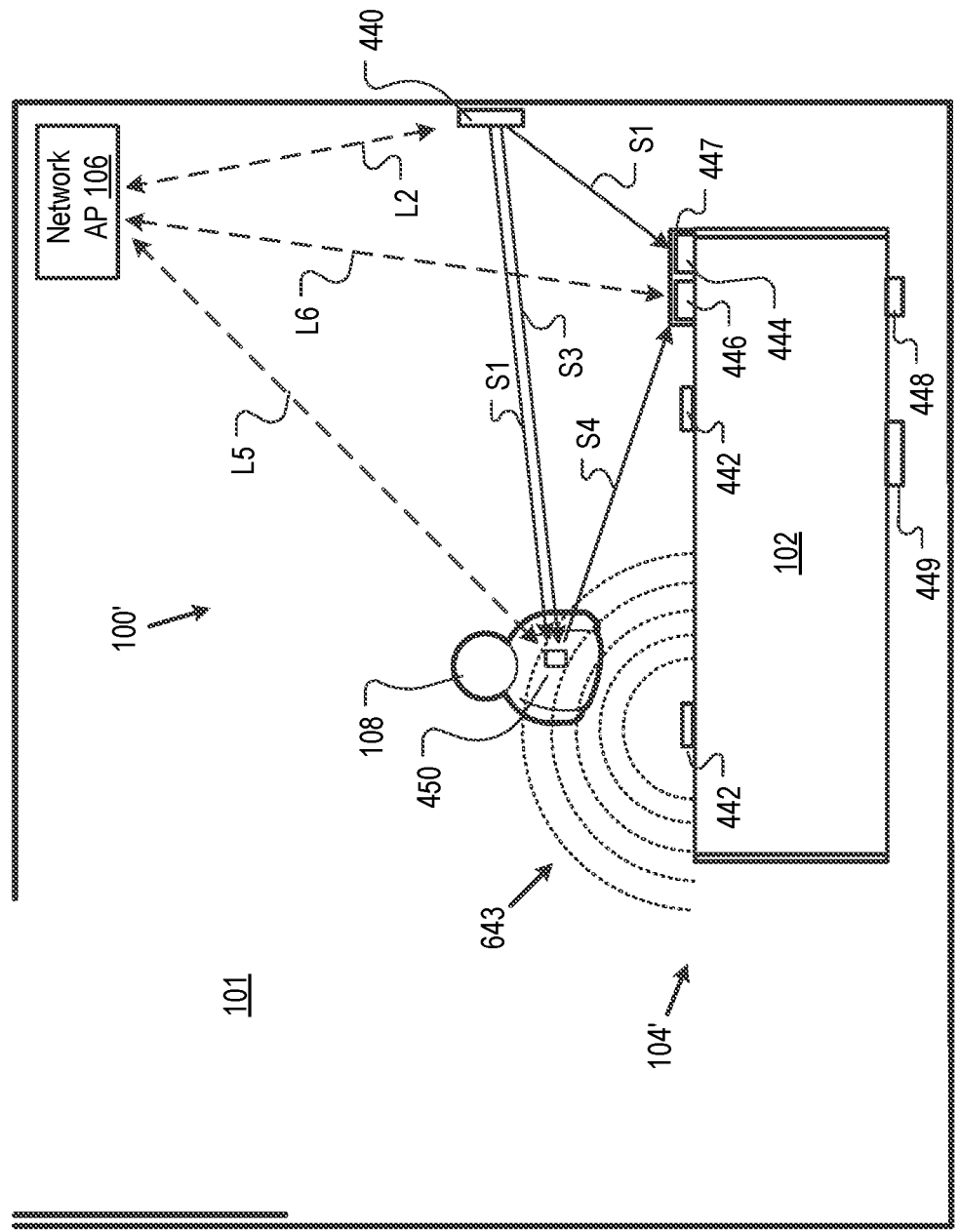
FIG. 6B depicts signaling for the embodiment depicted in FIG. 4 when a communications tag is within a threshold region.

Referring now to FIG. 6B, in some embodiments, when the distance between tag 450 and IR/US emitter 440 is below a threshold, for example 7 feet, SRD/IR device 447 commands one or more LF exciter 442 to emit LF. When tag 450 detects LF field 643, it reports such detection to SRD/IR device 447 via signal S4. The LF field emanates for only about 2 to 3 feet; thus, when the field is detected, the tag/caregiver will be quite close to bed 102. At such proximity, certain actions may be taken by the system. For example, in some implementations, bed controller 448 sends a control signal to actuator 336 (FIG. 3) to release the lock on bed rails 334 (FIG. 3). In various implementations of this embodiment, the decision to release the lock can be made by tag 450, or SRD/IR device 447, or bed controller 448. Also, rather than activating a hygiene alert in the less than 15 feet but greater than 7 feet proximity, in some implementations, an alert pertaining to hygiene is only activated when the LF field is breached; that is, if the caregiver/tag is within 2-3 feet.

It is notable that system 100' is not estimating distance in conjunction with LF exciters 442; the tag is simply detecting the field and, once detected, the system is taking action. The other communications (i.e., signals S1, S3, L2, L5, and L6) continue as appropriate. Also, those skilled in the art will appreciate that when system 100' is estimating distance via ultrasound, it is not estimating the distance from tag 450 to the bed, but rather to IR/US emitter 440. Therefore, the actions taken by the system based on the aforementioned threshold distances incorporate assumptions about the tag's position in the room (e.g., its proximity to the bed, etc.).

In some embodiments, the periodicity of the IR and US transmissions is about once per 1.5 to 3 seconds. This relatively low rate provides ample time for system 100' to decode the room ID, determine proximity of tag 450, and enable activation of non-immediate functions such as call cancellation. On the other hand, the transmission rate of LF exciters 442 must be very high, since the LF-field emanating therefrom extends only 2 to 3 feet from the bed. As such, activation and alerts responsive to detection of the LF field must be essentially immediate (a fraction of a second). In some embodiments, the transmission rate of the LF exciters is less than 500 milliseconds.

Figure 7:
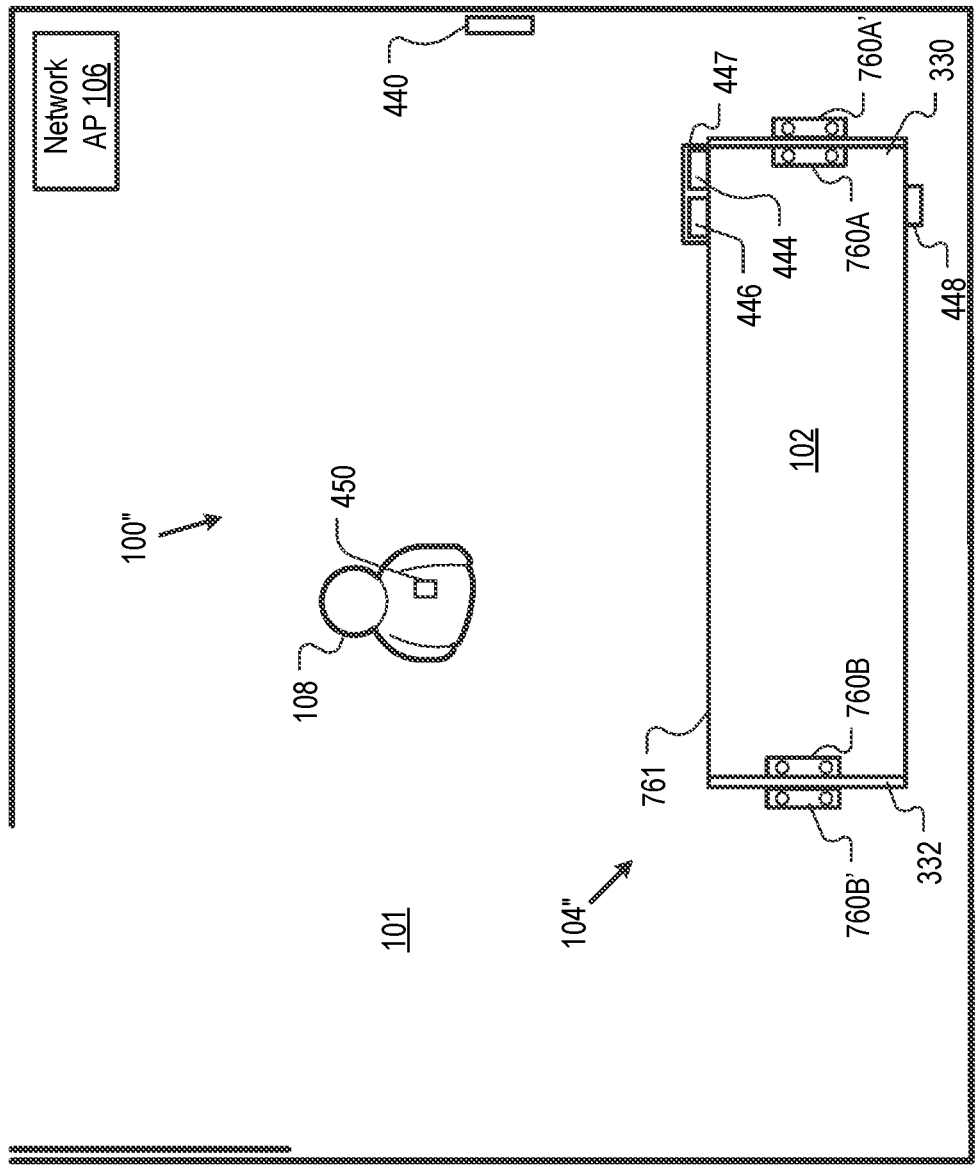
FIG. 7 depicts a second embodiment of the article of FIG. 1.

FIG. 7 depicts apparatus 104'', comprising bed proximity-determining system 100'' and bed 102. This embodiment of the bed proximity-determining system includes IR/US emitter 440, IR receiver 444, SRD device 446, bed controller 448, tag 450, and four pairs of US transmitters 760A, 760A' and 760B, 760B'. In the illustrative embodiment, IR receiver 444 and SRD device 446 are integrated in SRD/IR device 447. In the embodiment depicted in FIG. 7, IR receiver 444, SRD device 446, bed controller 448 and pairs of US transmitters 760A, 760A', 760B, and 760B' are bed-side components 210. IR/US emitter 440 and tag 450 are room-side components 220.

In the illustrative embodiment, US transmitter pairs 760A and 760A' are physically coupled to, and parallel with respect to, headboard 330. US transmitter pair 760A is disposed on the "front" side of headboard 330 and US transmitter pair 760A' is disposed on the "back" side of headboard 330. Similarly, US transmitter pairs 760B and 760B' are physically coupled to, and parallel with respect to, footboard 332. US transmitter pair 760B is disposed on the "front" side of footboard 332 and US transmitter pair 760B' is disposed on the "back" side of footboard 332. In some embodiments, the US transmitter pairs are disposed on top of headboard 330 and footboard 332, facing in opposite directions.

As explained in further detail in conjunction with FIGS. 8-11, in bed proximity-determining system 100'', one of the US transmitter pairs 760A, 760A', 760B, and 760B' is used to determine the distance between tag 450 and long-edge 761 of bed 102, which is the edge closest (i.e., the forward edge of the bed) to approaching caregiver 108. Because of the directional nature of ultrasound, which is usually about +/−50 degrees, and to ensure that line-of-sight between the tag and the US transmitters are not blocked (such as if a patient were sitting up in bed), two pair of US transducers are used at each end of the bed, one facing "outward" and the other "inward."

Figure 8:
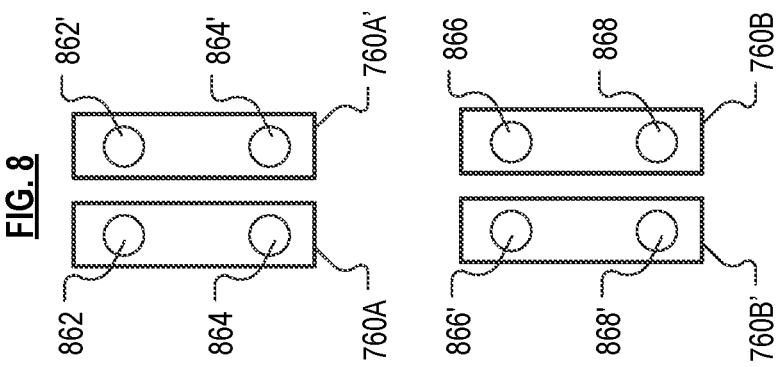
FIG. 8 depicts ultrasound transmitters for use in the embodiment of FIG. 7.

FIG. 8 depicts further detail of the US transmitter pairs. As depicted in FIG. 8, US transmitter pair 760A includes US transmitters 862 and 864, and US transmitter pair 760A' includes US transmitters 862' and 864'. Similarly, US transmitter pair 760B includes US transmitters 866 and 868, and US transmitter pair 760B' includes US transmitters 866' and 868'. As arranged on headboard 330, the distance between tag 450 and the two US transmitters in any of the pairs will always be different from one another. That is, for any location of tag 450, the distance between the tag and US transmitter 862 and the distance between the tag and US transmitter 864 is different. As explained further in conjunction with FIGS. 10 and 11, this is necessary for the proximity calculation. However, as will become clear from FIGS. 10 and 11, only one pair of US transmitters (i.e., two US transmitters) are required for determining distance.

There are certain advantages to a purely ultrasound solution for proximity determination, as compared to using LF as in bed proximity-determining system 100'. In particular, the LF field generated by the LF exciters of bed proximity-determining system 100' has a circular pattern, such that distance determination is problematic. Furthermore, hospital beds are often made of metal, which is not compatible with LF.

Figure 9:
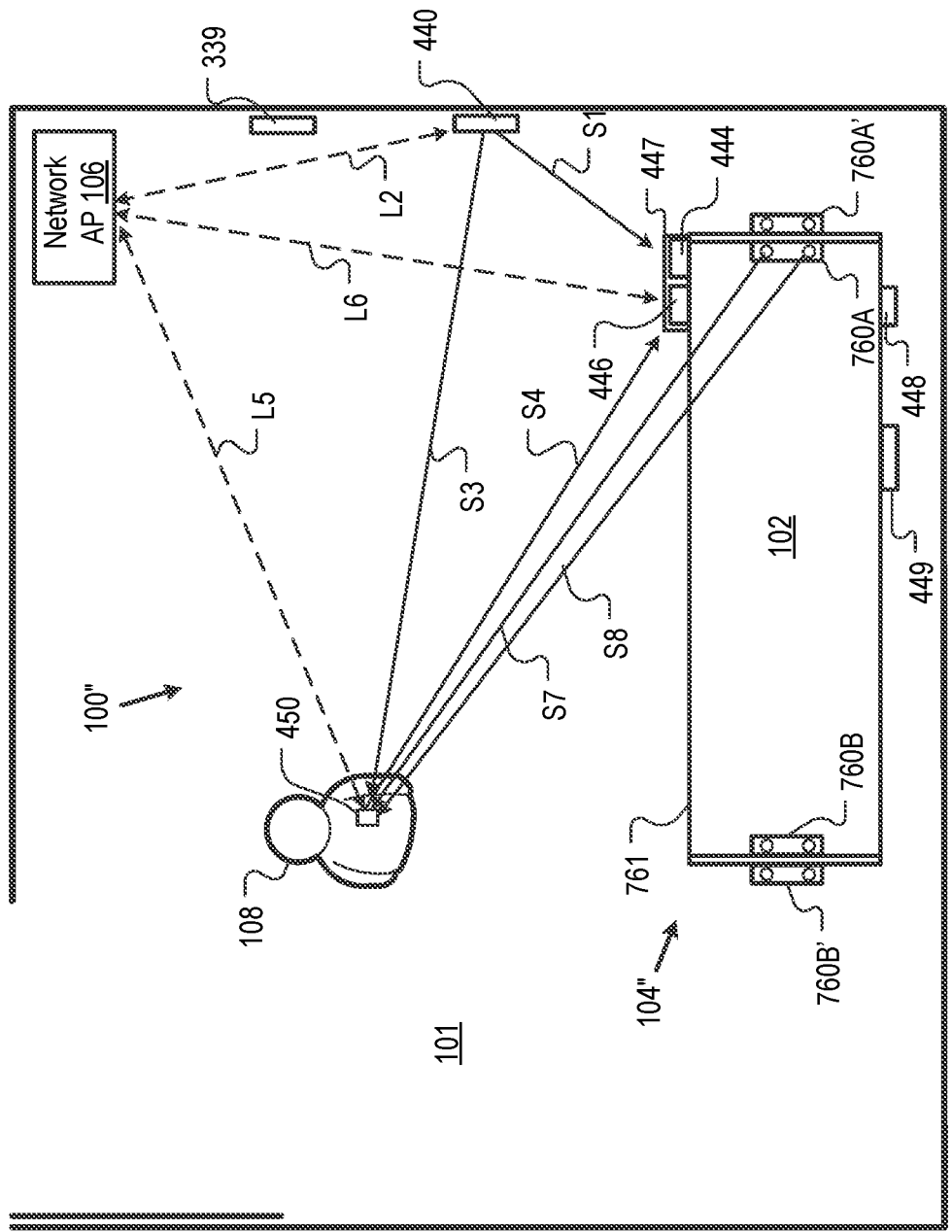
FIG. 9 depicts signaling for the embodiment depicted in FIG. 7.

FIG. 9 depicts the signaling occurring in conjunction with use of bed proximity-determining system 100''.

As in the previously discussed embodiment, the ID associated with the room that is carried via IR signal S1 from IR/US emitter 440 is detected by SRD/IR device 447. In some embodiments, SRD/IR device 447 reports the association of the bed with the ID to the local network via network AP 106 over communications link L6.

Timing information, such as provided, for example, from the local network to SRD/IR device 447 via link L6, or from the local network to IR/US emitter 440 via link S2 and from there to SRD/IR device 447 via signal S1, etc., initiates ultrasound signaling from the four pairs of US transmitters 760A, 760A', 760B, and 760B'.

In some embodiments, the US transmitter on each pair closest to forward edge 761 of the bed (i.e., US transmitters 862, 862', 866, and 866') transmit a signal (burst) at the same time. After a period of time long enough to ensure that the first burst of US signals have died (e.g., about 40 mS), an ultrasound burst is emitted from the other US transmitter of each pair. For clarity, the US transmissions from only one US transmitter pair are depicted. That is, ultrasound burst S7 from US transmitter 862 and ultrasound burst S8 from US transmitter 864 of transmitter pair 760A are transmitted, and received by tag 450. As discussed in conjunction with FIG. 10, this methodology enables calculating the distance to the closest plane; ultrasound from transmitters that are farther away than the closest transmitters to the tag will arrive later and are ignored. Another methodology allocates different time slots to the different pair of US transmitters. In some implementations, the distance calculated by tag 450 is reported to SRD/IR device 447 via signal S4. Alternatively, tag 450 can report to SRD/IR device 447 using the local network via links L5 and L6. Or, as previously disclosed, tag 450 can report information that enables other suitably programmed devices, such as SRD/IR device 447, bed controller 448, etc., to perform the distance estimate.

It is notable that in this embodiment, IR is emitted from IR/US emitter 440 at relatively low rate (c.a. 1.5-3 seconds). In some embodiments, to facilitate a high rate of US transmissions, the US transmitters transmit every 50 mS between each IR transmission. Tag 450 is capable of resolving US bursts that are associated with the same event (emission) and US bursts that are associated with different events (emissions). For example, in some embodiments, the first time slot after tag 450 receives an IR transmission is associated with all four of the US transducers closest to forward edge 761 of the bed (the "first set" of US transmitters). The second time slot, 50 mS after the first one, is associated with the other four ("second set") of US transmitters. The third-time slot will start after 100 mS, again with bursts from the first set of US transmitters, and so forth. In some implementations, tag 450, knowing the time of IR reception (i.e., when signal S3 is received), calculates the distance. For example, if IR is transmitted every 1.5 seconds, and the time slots are 50 mS apart, there are 15 opportunities (two 50 mS time-slots needed for each measurement) to determine the distance between tag 450 and bed 102. This high rate is very important for quick response and providing a fast-acting system.

Figure 10:
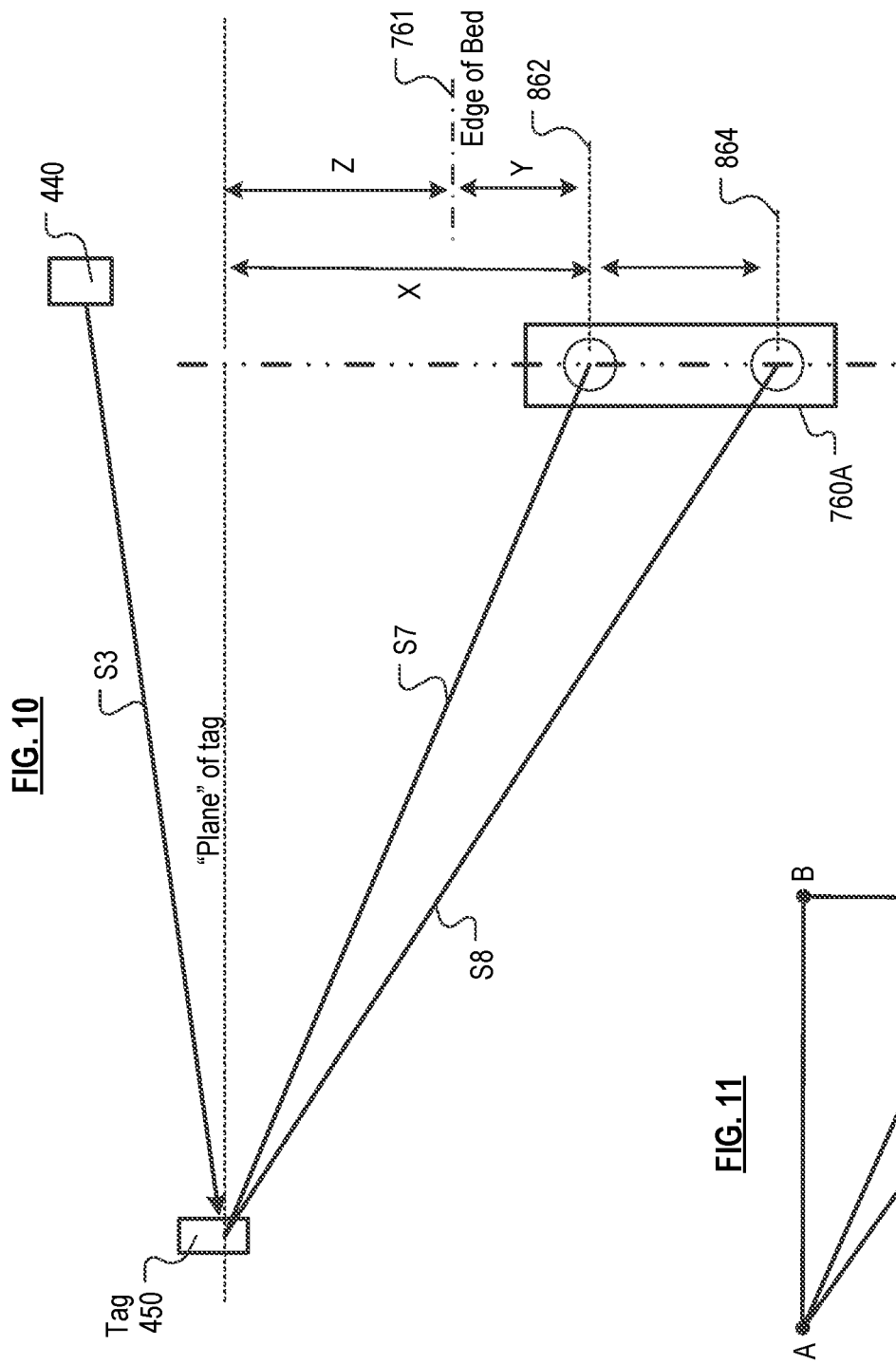
FIG. 10 depicts a method for determining orthogonal distance between a tag and a bed.
Figure 11:
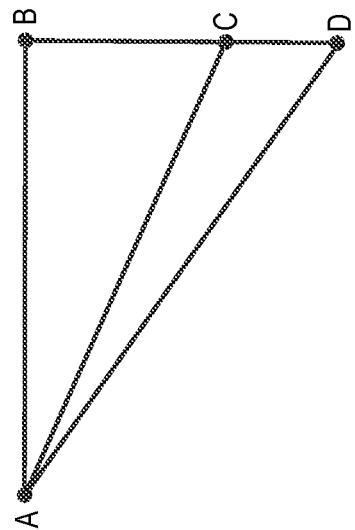
FIG. 11 depicts further details of the method of FIG. 10.

Referring now to FIGS. 10 and 11, a method for calculating distance from IR and US is depicted. The method can be used to determine the orthogonal distance between tag 450 and forward edge 761 of bed 102.

FIG. 10 depicts tag 450 and US transmitter pair 760A, wherein ultrasound burst S7 is transmitted from US transmitter 862 and ultrasound burst S8 is transmitted from US transmitter 864 as in FIG. 9. As can readily be seen from FIG. 11, two "right triangles" can be formed from the arrangement of FIG. 10, one comprising the sides AD, DB, and BA, and another comprising the sides AC, CB, and BA. Knowing the start time of US transmissions S7 and S8 (for example, based on the time that IR signal S3 is received), as well as the time that it receives transmissions S7 and S8, and any predetermined delay between IR transmission and US transmissions, tag 450 can determine the distance traveled by ultrasound transmissions S7 and S8. Relating this to FIG. 11, the length of sides AD and AC are therefore known. And since the distance between US transmitters 862 and 864 is known, so is the length of side DC.

Using the Pythagorean theorem, the orthogonal distance between tag 450 and forward edge 761 of the bed is determined. Thus, for the two right triangles of FIG. 11:

$$BA^2+DB^2=AD^2 \text{ and } BA^2+CB^2=AC^2 \qquad [1]$$

Rearranging to solve for common side BA:

$$AD^2-DB^2=BA^2 \text{ and } AC^2-CB^2=BA^2 \qquad [2]$$

From expression [2]:

$$AD^2-DB^2=AC^2-CB^2 \qquad [3]$$

From FIG. 11:

$$DB=DC+CB \qquad [4]$$

Substituting into expression [3]:

$$AD^2-(DC+CB)^2=AC^2-CB^2 \qquad [5]$$

Simplifying and rearranging expression [5] to solve for "CB":

$$CB=(AD^2-DC^2-AC^2)/(2DC) \qquad [6]$$

As depicted in FIGS. 10 and 11, side CB represents the orthogonal distance between US transducer 862 and tag 450 (shown in FIG. 10 as "X"). Knowing the distance between US transducer 862 and edge of the bed 761 (shown in FIG. 10 as "Y") and subtracting that from X yields the orthogonal distance Z between tag 450 and forward edge of the bed 761.

There are other bed-based functions that could potentially be controlled via a modified version of this system. For example, in modified versions of the system, functions of an appropriately configured bed that can be controlled include, without limitation, one or more of the following: raising/lowering segments of the mattress-support platform, locking/releasing a wheel brake, activating a weigh scale, extending/retracting a foot extension.

In one such embodiment, the modification includes a voice-controlled intermediary device. This intermediary device, which is carried by the caregiver, receives voice commands from the caregiver and then transmits the commands (in appropriate form) to the tag. The tag, in turn, transmits the commands (in appropriate form) to the bed, either through an existing network by transmitting to network AP 106, or by transmitting directly to a SRD/IR device or bed-controller on or near the bed.

In some embodiments, the intermediary device includes: (1) a microphone for receiving voice commands, (2) a processor running specialized software including: (a) voice-recognition software and (b) software capable of converting voice commands to signals suitable for transmission to the tag and for the tag to relay (or interpret and appropriately modify before relaying) to the bed for controlling bed functions, and (3) a transmitter for transmitting to the tag. In some other embodiments, the functionality of the voice-controlled intermediary device is incorporated into the tag itself.

In some embodiments, the voice-control function is not active until the tag determines that it is within a certain proximity from the bed, using the aforementioned techniques.

The appended claims should not be read as limited to the described order or elements unless stated to that effect. In addition, use of the term "means" in any claim is intended to invoke 35 U.S.C. § 112, 16, and any claim without the word "means" is not intended to do so.

It is to be understood that the disclosure describes a few embodiments and that many variations of the invention can easily be devised by those skilled in the art after reading this disclosure and that the scope of the present invention is to be determined by the following claims.

What is claimed is:

1. An apparatus comprising a bed proximity-determining system, the bed proximity-determining system comprising:
   a first infrared transmitter for transmitting an infrared signal, wherein the first infrared transmitter is associated with and is physically coupled to a surface of a room;
   one or more ultrasound transmitters that transmit ultrasound;
   a tag, the tag having an IR receiver for receiving the infrared signal, an ultrasound receiver for receiving ultrasound from the one or more ultrasound transmitters, and a transmitter that transmits first proximity-related information based on the received ultrasound;
   a first transceiver that receives the first proximity-related information and either:
      (a) transmits the first proximity-related information, or
      (b) generates and transmits second proximity-related information that is based on the first proximity-related information; and
   a bed controller, wherein the bed controller receives the first proximity-related information or second proximity-related information, and performs at least one of the following actions:
      (a) generates a control signal based on the first or second proximity-related information;
      (b) generates a command based on the first or second proximity-related information; or
      (c) transmits the first or second proximity-related information.

2. The apparatus of claim 1 further comprising a bed.

3. The apparatus of claim 2 wherein the first transceiver and the bed controller are physically coupled to the bed.

4. The apparatus of claim 2 and further comprising a first infrared receiver that receives the infrared signal, wherein the infrared signal transmits an identifier of the room, and wherein the first infrared receiver associates the bed with the room.

5. The apparatus of claim 1 further comprising an LF exciter, and wherein the tag further comprises an LF receiver.

6. The apparatus of claim 1 wherein the first proximity-related information is an estimate of distance based on the received ultrasound and the received IR signal.

7. The apparatus of claim 6 wherein the first proximity-related information transmitted by the tag is the estimate of distance.

8. The apparatus of claim 7 wherein the first transceiver transmits the estimate of distance received from the tag.

9. The apparatus of claim 8 wherein the bed controller receives the estimate of distance from the first transceiver and generates the command therefrom.

10. The apparatus of claim 8 wherein the bed controller receives the estimate of distance from the first transceiver and generates the control signal therefrom.

11. The apparatus of claim 7 wherein the first transceiver receives the first proximity-related information from the tag and generates the second proximity-related information, wherein the second proximity-related information is the command.

12. The apparatus of claim 11 wherein the bed controller receives the command and generates the control signal therefrom.

13. The apparatus of claim 1 wherein the first transceiver transmits the second proximity-related information to at least one of a call system or a hygiene-alert system.

14. The apparatus of claim 1 wherein the bed controller generates the command and further wherein the bed controller transmits the command to a hygiene system.

15. The apparatus of claim 6 wherein the one or more ultrasound transmitters comprise a first ultrasound transmitter that is associated with and is physically coupled to the surface of the room.

16. The apparatus of claim 15 wherein the estimate of distance is a distance between the tag and the first ultrasound transmitter.

17. The apparatus of claim 2 wherein the one or more ultrasound transmitters comprises a pair of ultrasound transmitters, wherein the pair thereof is physically coupled to the headboard of the bed or the footboard of the bed.

18. The apparatus of claim 17 wherein the first proximity-related information is an estimate of distance, wherein the distance is an orthogonal distance between the tag and a forward edge of the bed.

19. An apparatus comprising a bed proximity-determining system, the bed proximity-determining system comprising:
   a first infrared transmitter for transmitting an infrared signal, wherein the first infrared transmitter is associated with and is physically coupled to a surface of a room;
   a first ultrasound transmitter that transmits ultrasound;
   an LF exciter, wherein the LF exciter emits an LF field;
   a tag, the tag having an IR receiver, an ultrasound receiver, a processor for determining a distance between the tag and the first ultrasound transmitter, an LF receiver that detects the LF field, and a transmitter that transmits at least one of:
      (a) the distance,
      (b) an indication that the LF field is detected,
      (c) a command based on the determined distance or the LF field detection.

20. The apparatus of claim 19 further comprising a bed.

21. The apparatus of claim 19 further comprising a first transceiver, wherein the first transceiver receives at least one of:
   (a) the distance,
   (b) the indication,
   (c) the command.

22. The apparatus of claim 19 further comprising a bed controller, wherein the bed controller receives at least one of:
   (a) the distance,
   (b) the indication,
   (c) the command.

23. A method comprising:
   transmitting, at a first time, an IR signal from an IR transmitter that is physically coupled to a first wall of a room;
   transmitting ultrasound, at a known time relative to the first time, from a US transmitter that is physically coupled to a second wall of the room;
   receiving, at a mobile tag, the IR signal and the ultrasound;
   determining a distance based on a time the IR signal is received and a time the ultrasound is received; and
   Issuing a command, wherein the command is based on the distance and results in at least one of the following:
      (a) actuation of a mechanism in a bed;
      (b) canceling a call;

(c) activation of an alert pertaining to hand hygiene; and
(d) none of (a) through (c).

24. The method of claim 23 wherein the first wall and the second wall are the same wall.

25. The method of claim 23 and further comprising:
emitting an LF field from an LF exciter disposed on or near a bed that is the room;
sensing, at the mobile tag, the LF field; and
wherein issuing the command further comprises issuing the command based on the tag having sensed the LF field.

26. A method comprising:
transmitting ultrasound from at least a first ultrasound transmitter and a second ultrasound transmitter, wherein the first and second ultrasound transmitters are either both located on a headboard of a bed within the room or both located on a footboard of the bed;
determining a distance based on a time an IR signal is received and a time the ultrasound is received; and
issuing a command, wherein the command is based on the distance and results in at least one of the following:
(a) actuation of a mechanism in a bed;
(b) canceling a call;
(c) activation of an alert pertaining to hand hygiene; and
(d) none of (a) through (c).

27. The method of claim 26 wherein the distance is an orthogonal distance between a mobile tag and an edge of the bed.

* * * * *